United States Patent
Breskin et al.

(10) Patent No.: US 6,694,171 B1
(45) Date of Patent: Feb. 17, 2004

(54) X-RAY IMAGING OF TUMORS WITH DEXTRAN CARRIER OF PLATINUM COMPOUNDS

(75) Inventors: Amos Breskin, Nes Ziona (IL); Rachel Chechik, Moshav Beit Hanan (IL); Zvi Paltiel, Nes Ziona (IL); Bilha Schechter, Rehovot (IL); Abraham Warshawsky, Rehovot (IL); Abraham Shanzer, Rehovot (IL); Michal Neeman, Mazkeret Batya (IL)

(73) Assignee: Yeda Research and Development, Rehovot (IL)

( * ) Notice: Subject to any disclaimer, the term of this patent is extended or adjusted under 35 U.S.C. 154(b) by 0 days.

(21) Appl. No.: 09/445,977
(22) PCT Filed: Jun. 15, 1998
(86) PCT No.: PCT/IL98/00282
§ 371 (c)(1), (2), (4) Date: Mar. 6, 2000
(87) PCT Pub. No.: WO98/57669
PCT Pub. Date: Dec. 23, 1998

(30) Foreign Application Priority Data

Jun. 15, 1997 (IL) .............................................. 121084

(51) Int. Cl.[7] .................................................. A61B 5/00
(52) U.S. Cl. ....................................... 600/431; 424/9.4
(58) Field of Search ........................... 600/431; 424/9.4, 424/9.43

(56) References Cited

FOREIGN PATENT DOCUMENTS

| EP | 0 190 464 A | | 8/1986 |
|---|---|---|---|
| WO | 9402068 | | 3/1994 |
| WO | 9417829 | | 8/1994 |
| WO | WO 94/17829 | * | 8/1994 |
| WO | 9423759 | | 10/1994 |
| WO | 9600079 | | 1/1996 |
| WO | WO 96/00079 | * | 1/1996 |
| WO | 9722879 | | 6/1997 |

OTHER PUBLICATIONS

Aboud–Pirak E. et al, Inhibition of human tumor growth in nude mice by a conjugate of doxorubicin with monoclonal antibodies to epidermal growth factor receptor. Proc. Natl. Acad. Sci USA 3778–3781, 1989.
Arap, W. et al, Cancer treatment by targeted drug delivery to tumor vasculature in a mouse model, Science 377–380, 1998.
Arnon, R. et al, The use of antibodies and polymers as carriers of cytotoxic drugs in the treatment of cancer. In: Horizons in Biochemistry and Biophysics, vol. 9, Palmieri, F.J. Wiley and Sons Ltd. (Eds), England, p. 33–56, 1989.
Brooks PC, Montgomery AMP, et al, Integrin alfa (V) beta (3) antagonists promote tumor–regression by inducing apoptosis of angiogenic blood vessels, Cell 79: 1157–1164, 1994.
Folkman, J, Fighting cancer by attacking its blood supply, Sci Am 275:116–119, 1996.
Fujita T. et al, Control of in vivo fate of albumin derivatives utilizing combined chemical modification. J Drug Targeting 2: 157–165, 1994.
Hasida M. Nishikawa M. et al, Hepatic targeting of drugs and proteins by chemical modification, J Controlled Release 36:99–107, 1995.
Hurwitz, E. et al, Soluble macromolecules as carriers for daunorubicin, J Applied Biochem 2:25–35, 1980.
Johnson RC, et al, Lung endothelial dipeptidyl peptidase IV is an adhesion molecule for lung–metastatic rat breast and prostate carcinoma cells, J Cell Biol 121:1423–1432, 1993.
Johnston GI, et al, Cloning of GMP–140, a granulate membrane protein of platelets and endothelium: sequence similarity to proteins involved in cell adhesion and inflammation. Cell 56: 1033–1044, 1989.
Kikutani H. et al, Molecular structure of human lymphocyte receptor for immunoglobulin E. Cell 1986, 47: 657–665, 1986.
Lasky LA, et al, Cloning of a lymphocyte homing receptor reveals a lectin. Cell 56: 1045–1055, 1989.
Matsumura Y. et al, A new concept for macromolecular therapeutics in cancer chemotherapy: mechanism of tumoritropic accumulation of proteins and antitumor agent Smancs. Cancer Research 46:6387–6392, 1986.
Monsigny M. et al, Glycoconjugates as carriers for specific delivery of therapeutic drugs and genes. Adv Drug Dliv 14:1–24, 1994.
Neurath R. et al, Blocking of CD4 cell receptors for human immunodeficiency virus type 1 (HIV–1) by chemically modified bovine milk proteins: Potential for AIDS prophylaxis, J. Molec Recog 8:304–316, 1995.
Pasqualini R., et all Organ targeting in vivo using phage display peptide libraries. Nature 380:364–366, 1996.
Pimm MV, et al, Gamma Scintigraphy of the biodistribution of $^{123}$I–labeled N–(2–hydroxypropyl) methacrylamide copolymer–doxorubicin conjugates in mice with transplanted melanoma and mammary carcinoma, J Drug Target 3:375–383, 1996.

(List continued on next page.)

Primary Examiner—Ruth S. Smith
(74) Attorney, Agent, or Firm—Katten Muchin Zavis Rosenman

(57) ABSTRACT

A delivery system and method for targeting a contrast agent to tissues and organs for improved diagnosis of tumors and for prognosis and follow-up of cancer therapy by X-ray imaging. The delivery system includes a conjugate or complex of a macromolecular carrier and a contrast agent selected from the group consisting of: (a) a compound having a heavy element with an atomic number in the range of 75 to 92, and (b) a compound having an element with a property of an abrupt change in its X-ray attenuation coefficient within the energy range used for radiography, said macromolecular carrier of said conjugate or complex being optionally linked to a specific tissue marker molecule.

29 Claims, 7 Drawing Sheets

OTHER PUBLICATIONS

Pokutta S. et al, Conformational changes of the recombinant extracellular domain of E–cadherin upon calcium binding. Eur J. Biochem 223: 1019–1026, 1994.

Schechter B. et al, Liver accumulation of TNP–modified streptavidin and avidin: Potential use for targeted radio–and chemotherapy. J. Drug Targeting 4:171–179, 1996.

Schechter B. et al, Cis–platinum (II) complexes of carboxymethyl–dextran as potential anti–tumor agents. I. Preparation and characterization. Cancer Biochem. Biophys 8:277–288, 1986.

Schechter B. et al, Cis–platinum (II) complexes of carboxymethyl–dextran as potential anti–tumor agents. II. In vitro and in vivo activity, Cancer Biochem Biophys 8:289–298, 1986.

Schechter B. et al, Increased therapeutic efficacy of cis––platinum complexes of poly–L–glutamic acid against a murine carcinoma. Int. J Cancer 39:409–413, 1987.

Schechter B. et al, Selective cytotoxicity against tumor cells by cis–platin (II) complexed antitumor antibiotics via carboxymethyl dextran. Cance Immunol Immunother 25: 225–, 1987.

Schechter B. et al, Blood levels and serum protein binding of cis–platinum (II) complexed to carboxymethyl–dextran. Cancer Chemother Pharmacol 24: 161–166, 1989.

Schechter B. et al, Soluble polymers as carriers of cis–platinum. J Controlled Release 10:75–78, 1989.

Schechter B. et al, Indirect immunotargeting of cis–Pt to human epidermoid carcinoma KB using the avidin–biotin system, Int J Cancer 48: 167–172, 1991.

Schechter B. et al, Polymers in drug delivery: immunotargeting of carrier–supported cis–platinum (CDDP) complexes. Reactive Polymers 25:167–175, 1995.

Spiess M. et al, Sequence of human asialoglycoprotein receptor cDNA. J Biol Chem. 260: 1979–1982, 1985.

Taylor ME, et al, Contribution to ligand binding by multiple carbohydrate–recognition domain in the macrophage mannose receptor. J. Biol Chem. 267:1719–1726, 1992.

Schechter B et al: "Polymers in Drug Delivery: Immunotargeting of Carrier–Supported Cis–Platinum Complexes" Reactive Polymers, vol. 25, No. 2/03, Jun. 1995, pp. 167–175.

Avichezer D et al: "Functional polymers in drug delivery: carrier–supported CDDP (cis–platin) complexes of polycarboxylates—effect on human ovarian carcinoma" Reactive & Functional Polymers, vol. 36, No. 1, Feb. 1998, p. 59–69.

Knebel, Norbert G. et al: "2–Phenylindole–linked (2–(aminoalkyl) pyridine) dichloroplatinum (II): complexes with a selective action on estrogen receptor positive mammary tumors" J. Med. Chem., 1991, 34, 2145–52.

* cited by examiner

FIG. 7A
FIG. 7B

X-RAY IMAGING OF TUMORS WITH DEXTRAN CARRIER OF PLATINUM COMPOUNDS

FIELD OF THE INVENTION

The present invention relates to delivery systems for targeting contrast agents for improved diagnosis of tumors by X-ray imaging and to methods for diagnosis, prognosis and follow-up of treatment of tumors comprising administration of the delivery systems to patients followed by X-ray imaging.

BACKGROUND OF THE INVENTION

Although treatment of breast carcinoma, the most common malignancy among women, is improving steadily by means of surgical intervention and chemotherapy, prognosis depends heavily on early detection. In most developed countries, women aged 40–50 are urged to undergo annual mammography examinations. Ever since it was first introduced, mammography has improved in terms of its spatial resolution and the decrease in the required radiation dose. Yet there are limits on the size of detectable lesions, within permissive radiation doses, that are dictated by the very small density differences between malignant and normal tissues. Even the most advanced mammographic apparatus are limited in their tumor identification capacity. Although anatomical details are clearly portrayed, unequivocal identification is sometimes difficult.

The selective delivery of agents to specific organs is intended in general to specifically localize a delivered agent in the target organ while maintaining low levels in blood and other organs. Ideally, a targeting vehicle, e.g., antibody, which binds selectively to eptopes on specific cells, may be used for targeted delivery of therapeutic or diagnostic agents. Antibody-mediated delivery is, however, often restricted by lack of good antibody specificity (suitable antibodies for breast carcinoma are not available at present but they exist for other organs), limited specific uptake by the target tissue, low penetration and high prolonged levels in blood and other organs (Epenetos et al,1986; Welch, 1987).

Various other strategies have been developed for drug targeting, some of which are based on carrier-mediated delivery which employ natural ligands recognized by receptors or target cells. Most of these systems utilize macromolecular carriers armed with targeting ligands recognized by specific cell types. Certain targeting ligands are known, the most common are terminal saccharide residues recognized by receptors on liver parenchymal (Gal and GalNac of asialoglycoproteins, Ashwell et al, 1982) and non-parenchymal cells (GluNac and Man, Taylor et al, 1992), B-cells (Lasky et al, 1989) or endothelial cells (Bevilacqua et al, 1989). Recent developments in peptide chemistry and molecular biology yielded diverse peptide libraries consisting of numerous random peptide sequences (Pasqualini et al, 1996). Peptides with specific biological activity capable of mediating selective localization in tissues such as lung (Johnson et al, 1993) or lymphocytes (Cepek et al, 1994) have been obtained. An important example is the recently reported families of angiogenesis suppressing/inducing integrins that suppress or encourage the generation of new blood vessels (Varner et al, 1996; Folkman, 1996). These proteins are adhesion receptors not present in normal tissue but appear on endothelial cells of blood vessels of neovasculating areas. Since neovascularization is typical of malignant tissues at a certain stage, substances that interact with integrins might be considered as tissue markers for contrast agent delivery to blood vessels in neovasculating tumors (Brooks et al, 1994; Arap et al, 1998). Systematic screening of chemically-modified proteins (Neurath et al, 1995; Fujita et al, 1994) also yielded products recognized selectively by specific cells, for example, aromatic acid anhydrides that block CD4 cell receptors for HIV-1. Several systems were described that utilize macro-molecular carriers armed with targeting ligands recognized by specific cell types (Monsigny et al, 1994; Hashida et al, 1995).

Tissue-targeting research and practice also utilize several alternative approaches. Some rely on physiochemical properties leading to passive uptake and accumulation, such as inherent accumulation of the agent by the target tissue (e.g., iodine by the thyroid). An important mechanism is the enhanced permeability and retention (EPR) phenomenon whereby molecules of a certain size may diffuse through blood vessels in areas of neovascularization as in malignant tissues (Matsumura et al, 1986; Duncan et al, 1996). Although this mechanism is not specific in terms of organ and type of the malignancy, a contrast agent may be delivered to all neovasculating lesions by means of EPR, thus providing important pathological and anatomical information for many types of tumor.

The intense activity in the field of targeting drugs to specific organs, tissues or cells have yielded a variety of carrier systems such as pro-drugs, liposomes, e.g., sterically stabilized liposomes (SSL) (Kedar et al, 1994) or polymers, both natural and synthetic. The carrier conveys the drug to the specific tissue (via antibody or a tissue marker) where the drug executes the therapy. Attempts to use selective delivery for diagnosis by targeting contrast agents are not as common, though MRI or sonographic agents are under examination. On the other hand, scintigraphy, based on the accumulation of radioisotopes in particular organs or in cancer lesions, is commonly practiced in clinics. X-ray absorbing agents, such as barium and iodine, are being used routinely in non-specific administration.

Citation of any document herein is not intended as an admission that such document is pertinent prior art, or considered material to the patentabilty of any claim of the present application. Any statement as to content or a date of any document is based on the information available to applicants at the time of filing and does not constitute an admission as to the correctness of such a statement.

SUMMARY OF THE INVENTION

It is an object of the present invention to provide a delivery system and a method for tumor diagnosis, prognosis and follow-up of cancer therapy by using macromolecular carriers with or without specific tissue markers, for delivering heavy metals with an atomic number (hereinafter indicated by "Z") within the range 75–92, to selected organs or sites for tumor-enhanced X-ray imaging.

Another object of the present invention is to use the same delivery system and method for delivering lower Z elements which have the property of an abrupt discontinuity/change in their X-ray attenuation coefficients, and whose attenuation threshold is within the X-ray energy range used for the specific radiography technology selected (e.g., mammography, computed tomography, digital radiography). Thus, the images obtained from two parts of the X-ray energy spectrum, one above the threshold and one below the threshold, can then be used to digitally generate a difference image having superior contrast. The two images can be generated either by filtering the impinging radiation or by analyzing the detected radiation according to the above threshold and the below threshold contributions. All elements with Z in the range of 33–50 progressively exhibit such a discontinuity/change in X-ray attenuation coefficient in the 10–30 keV range within which all mammography is applied.

The present invention thus relates to a delivery system for targeting a contrast agent to specific organs for the purpose of tumor diagnosis, prognosticating the effectiveness of chemotherapy in treating cancer and for follow-up of cancer therapy by X-ray imaging, where the delivery system includes a conjugate or complex of a macromolecular carrier and a contrast agent selected from: (a) a compound of a heavy element with an atomic number in the range of 75–92, and (b) an element with a property of an abrupt change in its X-ray attenuation coefficient within the energy range used for radiography, where the macromolecular carrier may be optionally linked to a specific tissue marker.

The present invention further relates to methods for tumor diagnosis, for prognosticating the effectiveness of chemotherapy in the treatment of cancer, and for follow-up of cancer therapy by X-ray imaging, which involves administering to a patient an effective amount of a delivery system of the present invention, followed by X-ray imaging of the patient. As a non-limiting example, the delivery system is used for diagnosis, prognosis and/or follow-up of chemotherapy for breast cancer.

Abbreviations

The following abbreviations are used throughout the specification:
ADH: adiric acid hydrazide; BSA: bovine serum albumin; CDDP: cis-diamminedichloroplatinum II (cisplatin); CMdex: carboxymethyldextran; DDW: double-distilled water; EPR: enhanced permeability and retention; Hydr (H in the figures): hydrazine or hydrazide; OPDA: o-phenylenediamine; Ova: ovalbumin; St: streptavidin; TNP: 2,4,6-trinitrophenyl.

BRIEF DESCRIPTION OF THE DRAWINGS

In FIG. 4B, the molar ratio of ADH or hydrazine bound per CDDP was calculated from the absorbance presented in FIG. 4A. More efficient interaction was observed with hydrazine.

FIGS. 7A–7B show mammography film images of a mouse treated with Pt-loaded CMdex-Hydr, 12 hours post administration (FIG. 7A), and a control mouse treated by the same dextran derivative with no Pt load (FIG. 7B). The liver of the first mouse is darker and more clearly delineated, whereas that of the second mouse is indistinguishable from other organs.

DETAILED DESCRIPTION OF THE INVENTION

Figure 1:
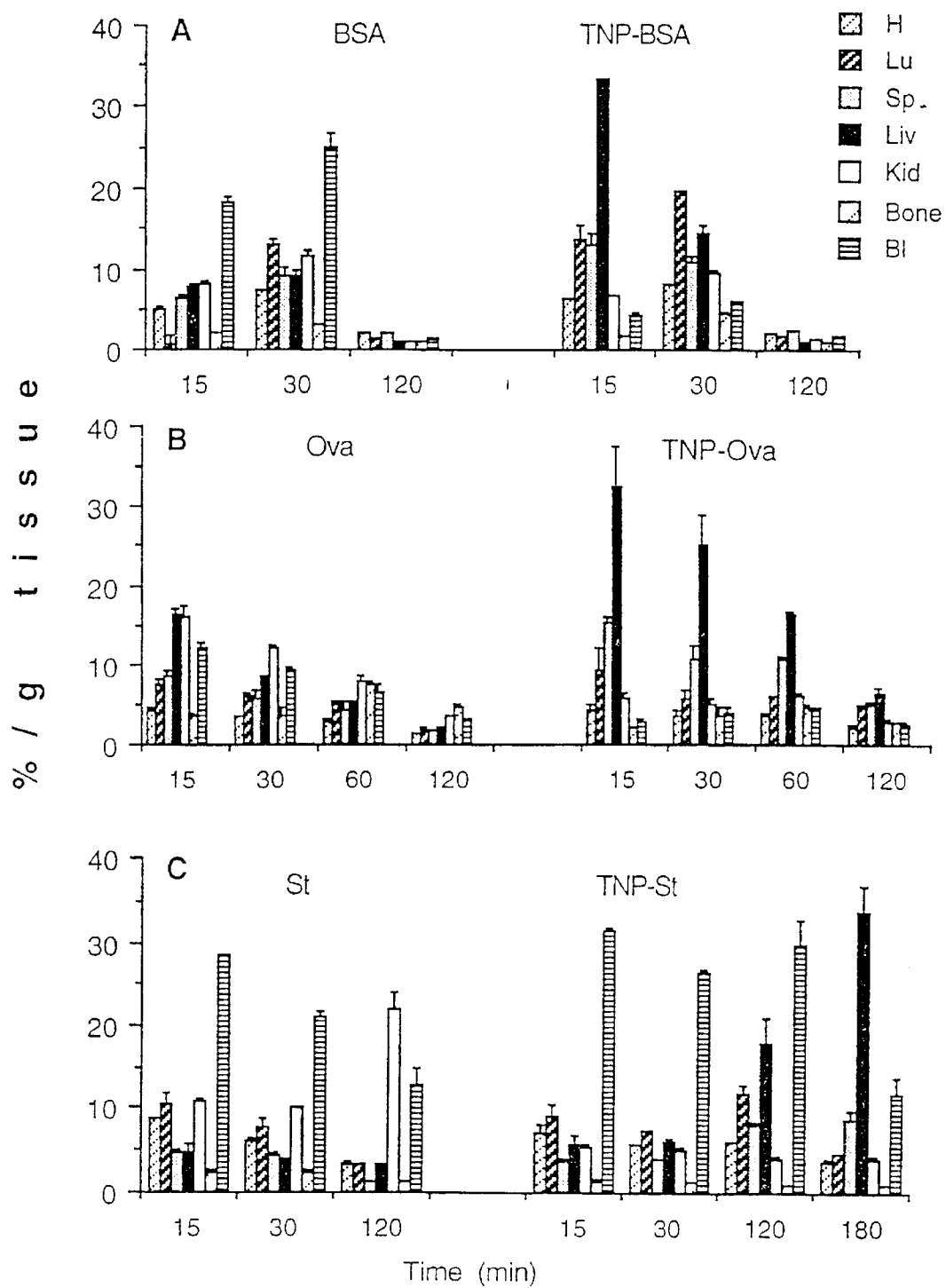
FIGS. 1A–1C show biodistribution (%/g tissue) of the radioiodinated degradable albumins BSA (FIG. 1A) and Ova (FIG. 1B) and the non-degradable St (FIG. 1C) with and without TNP modification (liver marker) in CD-1 male mice, as a function of time (15–120 min) following Intravenous injection. Levels of the native BSA, Ova and St and the modified TNP-BSA, TNP-Ova and TNP-St expressed as mean %/g tissue are depicted for blood (Bl) and six organs (heart, H; lung, Lu; spleen, Sp; liver, Liv; kidney, Kid; and bone).

The present invention was developed from a new concept based on simple physical principles relating to differential radiation attenuation by tissues of different densities. Such differences can be enhanced by chemical and biological means. The implementation of this concept of tumor-specific X-ray imaging, e.g., mammography, utilizes current radiographic equipment and will permit efficient tumor diagnosis, including population screening, with reduced radiation doses.

Physiological and pathological characteristics of an imaged tissue should offer vital information for tumor diagnosis. This is achieved according to the present invention by selectively loading the tumor with appropriate contrast agents through physiological processes or tissue-specific markers. For X-ray radiography, the best contrast materials are high atomic number (heavy metal) elements which exhibit strong X-ray attenuation. The success of such an approach depends on the possibility of selectively conveying significant amounts of the contrast agent into the cancerous tissue. To reach this goal, the present invention provides a delivery system in which selected contrast agents are bound to carrier molecules that specifically accumulate in the cancer tissue.

For breast cancer diagnosis, specific tissue markers are preferred for targeting breast tissue, but since there are currently no such satisfactory markers, the invention presently uses as a preferred embodiment the general enhanced permeability and retention (EPR) phenomenon (Matsumura et al, 1986), known to induce carrier-ligand Iaccumulation in neovasculating cancerous tissues (Duncan et al, 1996). The invention can also be used for tumor diagnosis in other tissues or organs, particularly when tissue-soecific markers are unavailable. The present delivery system, however, can further incorporate specific tissue markers when they are available for imaging of selected tissues or organs.

The delivery of contrast agents to specific organs may benefit from the vast information regarding targeting and controlled release of drugs for therapy. However, there are significant differences between the two systems due to the different requirements, as shown in Table 1.

TABLE 1

Drug Versus Contrast Agent Targeting

| | Drug Delivery | Contrast Medium Delivery |
|---|---|---|
| Release of Active Component | Required | Not Required |
| Intracellular Release | Often Required | Not Required |
| Controlled Release | Advantageous | Not Applicable |
| Long Maintenance | Advantageous | Not Advantageous |
| High Concentration within Tissue | Advantageous | Required |
| Repeated Administrations | Routinely (Often) | May Not Be Required |
| Attached Chemical | Chemotherapeutic Drug | Heavy Metal |
| Toxicity | Accepted up to a Certain Level | Unacceptable (for Screening) |
| Invasive Administration | Might Be Considered | Unacceptable |

A transport system which is inadequate for drug delivery may prove suitable for contrast agent transport. Thus, for example, conditions such as long maintenance, controlled and intracellular release of the active component are essential in drug targeting but are not required for diagnostics. On the other hand, a high concentration of the delivered agent for diagnostics is essential.

The purpose of the present invention is both to improve the delineation of small-size cancerous tissue and to provide a clear indication regarding its pathological status. These goals can be achieved by taking advantage of distinct functional and physiological properties of the cancerous tissue for targeting contrast agents, followed by X-ray imaging.

The delivery system according to the present invention, developed for delivering a contrast agent to a target tissue or organ for X-ray imaging, includes a conjugate or complex of a macromolecular carrier and a contrast agent, where a specific tissue marker can be optionally linked to the macromolecular carrier when available for a specific tissue or organ.

The contrast agent may be any non-toxic (in free or in bound form) organic or inorganic compound of a heavy element with atomic number Z=75–92, e.g., heavy metals such as Pt, Au, Tl, or alternatively, an element with an X-ray attenuation threshold in the relevant energy range for the specific radiography technology, e.g., Zr, in the case of mammography. At the X-ray attenuation threshold, there is an abrupt change or discontinuity in the X-ray attenuation coefficient with respect to X-ray energy. All elements with Z in the range of 33–50 exhibit such an X-ray attenuation threshold in the 10–30 keV X-ray energy range. When an energy range above 30 keV is used in radiography, an element with Z above 50 is used for its property of having an X-ray attenuation threshold in the appropriate X-ray energy range.

The heavy element is preferably a heavy metal selected from Pt, Au and Tl, and the macromolecular carrier is selected from liposomes and natural or synthetic polymers. The heavy metal compound may be attached to the natural or synthetic polymer through a metal-binding group or ligand containing nitrogen, nitrogen-oxygen or sulfur atoms, such as thiol, hydrazido, piperazirne and the like, or the heavy metal compound may be complexes to the polymer through a metal-chelating ligand, such as iminodiacetic acid, ethylene-diaminetetraacetic acid (EDTA), diethylenetriaminopentaacetic acid (DTPA), hydroxyquinoline, hydroxamic acids, hydrazides and the like, and combinations thereof.

Potential detection techniques include, but are not limited to, 2D digital radiography, CT, dual energy and image subtraction, "positive" and "negative" imaging, etc, all based or, X-ray attenuation in the imaged body. An X-ray detection means include X-ray filter and screen-enhanced film and digital X-ray detectors.

Selection of the appropriate contrast agent and its. delivery system is an apparent prerequisite according to the invention. Since there is a profound ncrease in X-ray attenuation with an increase of the atomic number (Z), it is advantageous to select heavy elements of Z=75–92 as preferred contrast agents rather than the more common iodine (I). Metals of choice are gold and platinum which are already in use in several pharmaceutical formulations. In case of dual energy, however, other elements having lower Z might be preferred, due to the abrupt change in their X-ray attenuation coefficient within the relevant energy interval.

The metal-loaded macromolecular carrier can be specifically targeted to certain types of cells, e.g., tumor cells, delineating primary tumor growth or tumor metastases by "positive imaging", or to the tumor-bearing organ, delineating tumor lesions by "negative imaging". Antibody-directed contrast agent targeting may be used wherever specific and effective antibodies are available.

Two types of macromolecular carriers can be used for heavy metal contrast agents according to the present invention. The first is a conjugate of the polymer with a metal binding ligand to which a heavy metal is attached. This general type is preferable for non-targeted delivery into cancerous sites by physical entrapment processes, such as those occurring in neovascularizatlon sites of tumors. The second type is a conjugate of the polymer with a targeting ligand (tissue marker), in addition to the metal binding ligand to which a heavy metal is attached. The role of the targeting ligand is to direct the whole conjugate to a specific tissue via the affinity interaction of the targeting ligand to a given epitope on the specific cell. Certain targeting ligands/tissue markers are known, as described in Table 2.

TABLE 2

Tissue Markers (Examples)

| Tissue | Marker | Reference |
| --- | --- | --- |
| Liver Hepatocytes (Asialoglycoprotein Receptor) | Gal, GalNac | Ashwell et al (1982) |
| Liver Kupffer Cells | Man, GluNac, Fuc | Taylor et al (1992) |
| B Cells (IgE Fc Receptor) | Gal | Kikutani et al (1986) |
| Leukocytes (L-selectin) | Fuc, Sialic acid | Lasky et al (1989) |
| Endothelial Cells (E-selectin) | Fuc, Sialic acid | Bevilacqua et al (1989) |
| Platelets (P-selectin) | Fuc, Sialic acid | Johnston et al (1989) |
| Lung and Liver Macrophages | Man, Fuc | Taylor et al (1992) |
| Lung | Endothelial Marker | Pokutta et al (1994) |
| Brain[1] | Ser-Arg-Leu (SRL) Containing Peptide | Pasqualini et al (1996) |
| Kidney Blood Vessels | CLPVASC Peptide | Pasqualini et al (1996) |
| Tumor Blood Vessels | Arg-Gly-Asp (RGD) and Asn-Gly-Asp (NGD) Containing Peptides | Arap et al (1993) |
| CD4 Cell Receptors for HIV-1 | 3-hydroxyphthalic and trimellitic anhydrides | Neurath et al (1995) |

[1]Many cell adhesion receptors recognize simple sequences that can be reproduced as synthetic peptides homing to these cells. Peptides capable of binding to cell adhesion receptors, such as integrins, can be used as mediators for cell or tissue targeting. Factors such as EGF, VEGF, MHS, etc. can also serve for specific tumor targeting to the specific receptors (for these factors) that are overexpressed on certain tumor cells.

A tissue marker in addition to those of Table 2, is the 2,4,6-trinitrophenyl (TNP) group, a targeting ligand to the liver. As described in Schechter et al, 1996, and in PCT Publication No. WO 97/22879 of the same applicants, TNP-streptavidin, obtained by reaction of ε-amino groups of lysine residues of streptavidin with 2,4,6-trinitrobenzenesulfonic acid (TNBS), accumulates mainly in the liver.

In order to select a suitable delivery system according to either type of targeting system described above, biodistribution of the metal-macromolecular carrier conjugate provides information regarding its specific sites of accumulation, metal uptake kinetics and saturation. To provide biodistribution data, the polymer, e.g. dextran or a dextran derivative such as CMdex or CMdex-hydrazide, is charged with several tyrosyl residues for radioiodination, the radiolabeled agent is then administered intravenously into mice, and at set time intervals, blood and organs are analyzed for biodistribution parameters (Schechter et al, 1996). Determination of the actual metal accumulation can be done by atomic absorption spectroscopy, XRF (X-ray fluorescence) and ICPS (inductively-couoled plasma spectroscopy) analysis of tissue samples. Experiments are directed at both tissue accumulation for "negative imaging" and tumor accumulation for "positive imaging".

The preferred systems for delivery of heavy metal contrast agents according to the present invention are macromolecules carrying a heavy metal as defined in the present invention. Such a macromolecule that will be defined for the purpose of this invention as a "macromolecular system" is composed of (a) a suitable macromolecular carrier, (b) a metal binding group as a pendant group, and (c) a heavy metal salt or complex. The metal salt or complex will be part of the macromolecular system due to attachment via the metal binding ligand. The scientific literature, including patents, teaches many ways to bind a metal salt or metal complex to a macromolecular carrier, including the present inventors' own publications (Warshawsky, 1980, 1982, 1984, 1986, 1987a, 1987b, 1987c) which show how to bind platinum and platinum group metal (including gold) to polymeric carriers. The literature also teaches us how to bind metal ions to polymers for pharmaceutical uses (Dunn et al, 1991). Of particular interest for the present invention are polymer carriers, such as, for example, carbohydrates, e.g. dextrans and modified dextrans such as carboxymethyldextrans, polyamino acids such as poly-L-lysine and polyglutamic acid, the polymers described in Duncan et al (1996) and Pimm et al (1996), polymers which display selective delivery or accumulation in the target tissue, e.g. polymethacrylic acid in neovasculating regions such as in tumors, as well as polymers modified with specific tissue markers, including address molecules with known tissue or organ specificity.

The present invention relies on the use of macromolecular carriers that are already described in the literature and are used in practice, provided that they conform to the criteria for contrast medium delivery described in Table 1 for diagnostic applications, particularly the criteria of high metal loading and very low systemic toxicity. The present inventors have found that, although sometimes the right compositions are known, they lack sufficient numbers of functional groups to allow binding of a sufficient amount of the heavy metal. The present invention shows how to achieve this high loading in the particular cases given. Other synthetic molecules of preselected shapes, such as liposomes or ball shaped structures such as "dendritic" structures, are also included. Such dendritic structures comprise a polymeric carrier such as carboxymethvldextran onto which radially branching appropriate bifunctional molecules, e.g. dicarboxylic acids and/or hydrazides thereof, are anchored, thus providing a way to increase the "per unit" loading of functional metal binding groups and allow for higher contrast agent load so that the total carrier dose can be decreased. It also provides for a way to control or manipulate the size and shape of the macromolecular system and to engineer optimal site-specific delivery by controlling the sieving effect as in neovascularization sites in active tumors.

Since no toxic side-effects are tolerable, particularly in large population screening, such as in mammography, stringent measures should be taken to ensure complete safety. Thus, the metal carrier agents according to the invention are characterized by high-affinity bound metals by chelates or non-dissociable binding, e.g., covalent binding, to prevent metal release. Preferred macromolecular carriers are those that form non-toxic conjugates or complexes with the metal. Ultimately removable or biodegradable polymers should be used to ensure limited in vivo residence time and complete clearance. The macromolecular carrier should not be toxic either by itself or in its conjugated or complexed form, and its properties should be a compromise between circulation of sufficient duration to allow accumulation at the tumor site prior to X-ray imaging and subsequent efficient removal to ensure limited in vivo residence time and complete clearance. For this purpose, suitable candidates are sterically stabilized liposomes and various macromolecules, such as dextrans and synthetic polymers, e.g., polymethacrylic acid, a polymer which has been studied thoroughly in targeted drug delivery and radioactive diagnostic research (Duncan et al, 1996; Pimm et al, 1996). The chemical binding between the contrast agent and the macromolecular carrier should be strong enough to prevent metal release to avoid the poisonous effects of the heavy metal and to allow high agent loading capacity to enable minimal carrier doses.

According to the present invention the amount of agent, e.g., gold or Pt, to be delivered to the tissue, required for sufficient contrast enhancement with current X-ray radiographic or tomographic equipment, is of the order of 100 $\mu$g/ml (or per gram tissue) or more. Depending on the efficiency of the targeting, this imposes a lower limit on the amount of agent the conjugate should contain. Considering the level of concentration reached in our preliminary experiments on a model system of liver targeting, i.e., 60–70% injected dose/ml tissue, the amount of agent in the conjugate should exceed 160 $\mu$g per injected dose. The actual amounts are to be adjusted according to the delivery system to be selected.

Based on our previous studies on carrier-mediated drug targeting (Schechter et al, 1986a, 1986b, 1987a, 1987b, 1989a, 1989b, 1991, 1995; Arnon et al, 1989), dextran was selected as a preferred multi-purpose carrier for tissue-specific targeting. Dextran is available in different molecular sizes, and it is characterized by high solubility in water, resistance to proteolytic degradation, and low immunogenicity. Dextran is also non-toxic, as known from extensive experience in clinical use of dextran as a plasma expander (Larsen, 1989), and can be chemically modified. For instance, dextran modified to the carboxymethyldextran form (CMdex; Hurwitz et al, 1980) is highly substituted with carboxyl groups that can be further derivatized with other groups. Dextran has been shown to be modified for attachment to antibodies in immunotargeting system (Schechter et al, 1987b; Arnon, 1989; Aboud-Pirak et al, 1989), to carry different drugs (Schechter et al, 1986a, 1986b, 1989a, 1995; Hurwitz et al, 1980; Bernstein et al, 1987), biotinyl groups in avidin-mediated procedures (Schechter et al, 1996, 1991) and tyrosyls for radioiodination (Schechter et al, 1996). Due to the abundance of functional groups, modified dextrans can serve as backbone carriers for chemical attachment of tissue markers and still carry enough groups for coupling or complexing the delivered agent.

One aspect of the present invention is aimed at preparing a targeting system for tissue-selective delivery of metals that can serve as contrast agents for X-ray radiography. Standard available radiographic techniques can be improved by conveying significant amounts of the contrast agent, preferably elements with high atomic numbers, such as Pt, into the cancerous tissue. This is expected to increase the density differences between malignant and normal tissue. Previous experience with Pt compounds or complexes between CDDP, a known chemotherapeutic drug, and macromolecular substances, e.g. CMdex (Schechter et al, 1986a, 1986b, 1987a, 1987b) enabled the present inventors to design a Pt-carrier system for contrast agent delivery. Such a delivery system is based on (a) a carrier, e.g. CMdex-hydrazide, enriched with functional groups to allow for heavy metal, e.g. Pt, loading capacity as well as tissue marker, e.g. TNP, conjugation; and (b) strong chemical binding between the metal and the carrier to prevent toxic metal release.

According to the present invention, the contrast agent delivery system is chosen so as to improve cancer detection capability of existing X-ray imaging techniques and procedures, and in order to provide higher tumor-specificity and better resolution. This should permit efficient detection of small cancer lesions at lower radiation doses.

The improvement of cancer detection capability by tumor-specific X-ray imaging according to the invention will lead to earlier and more conclusive diagnostic procedures for solid tumors that will have significant impact on the prognosis of patients and will permit more efficient non-invasive follow-up of cancer patients subjected to therapy as well as a better control of drug delivery to tumors.

Having now generally described the invention, the same will be more readily understood through reference to the following examples, which are provided by way of illustration and are not intended to be limiting of the present invention.

EXAMPLES

In the Examples, the following materials and methods are used:

MATERIAL AND METHODS i) Materials. Streptavidin (St) was provided as a gift from Boehringer-Mannheim GmbH (Mannheim, Germany), and CDDP from Abic Company (Ramat Gan, Israel). CMdex was prepared from dextran as previously described (Hurwitz et al, 1980). N-hydroxysuccinimide(NHS), 1-ethyl-3-(3-dimethyl-amino-propyl)-carbodiimide(EDC), 2,4,6-trinitrobenzenesulfonic acid (TNBS), dicyclohexylcarbodiimide (DCC), t-butyloxycarbonyl-tyrosine (BOC-Tyr), and 2-[N-morpholino]ethanesulfonic acid (MES) buffer were purchased from Sigma (St. Louis, Mo.). O-phenylenediamine (OPDA) was obtained from Fluka Ag (Buchs, Switzerland), and N,N-dimethylformamide (DMF) from Merck-Schuchardt (Munich, Germany).

CMdex Products: Dextran Mr-10, 20, 40, 70 or 250 was converted into the carboxymethyl form CMdex according to a procedure previously described for dextran Mr-40 (Hurwitz et al, 1980). Dextran was reacted with chloroacetic acid in a strongly basic solution and the products were analyzed by NaOH titration for the degree of carboxyl group content. Samples of the Na-salt derivatives obtained after synthesis (10 mg) were dissolved in 1 ml 0.3M HCl to convert the COONa groups into COOH, dialyzed against 2L double distilled water (DDW) and lvophilized. Dry samples of the Na-free products (5 mg), dissolved in 2 ml DDW, were titrated with 0.01M NaOH in the presence of phenolphthalein, and the carboxyl grouo content (carboxymethyl substitution) and the molecular weight of the CMdex derivatives were calculated (Table 3). Dextran Mr-10 gave rise to a 12.2 kDa CMdex product containing 0.63 carboxyl groups per glucose unit of 40 carboxyls per dextran. Ratios of carboxymethyl/glucose in the different preparations ranged between 0.38 to 1.2. CMdex Mr-20, 40, 70 and 250 contained 47, 275, 297 and 1875 carboxyl groups, respectively.

TABLE 3

| CMdex Mr-10, 20, 40, 70, 250 | | | |
|---|---|---|---|
| Dextran kDa | COOH/Unit | Unit Da | Cmdex KDa |
| 10 | 0.63 | 198 | 12.2 |
| 20 | 0.38 | 184 | 22.6 |
| 40 | 1.10 | 226 | 55.8 |
| 70 | 0.68 | 204 | 88 |
| 250 | 0.73 | 231 | 356 | ii) Preparation of CMdex-hydrazide (CMdex-Hydr). CMdex-hydrazide was prepared from dextran Mr-250 according to two different protocols. Protocol 1 produced a CMdex-hydrazide product containing many hydrazide and few free carboxyl groups and did not bind Pt well, while the product of Protocol 2 contained few hydrazido and many free carboxyl groups and bound Pt effectively.

Protocol 1: CMdex (30 mg) was dissolved in 0.15M MES buffer pH 5 (1.5 ml), and aqueous hydrazine (0.5 ml, 5M), adjusted to pH 6 with 6M HCl, was added. Then, EDC (53 mg×3 at 20 min intervals) was added while vortexing. After 7 hours at room temperature (RT), the solution was dialyzed against 2×4L DDW for 12 hours. The sample was then treated with 6M HCl (0.1 ml) and dialyzed as described above. The product CMdex-Hydr was obtained as 3.5 ml of a clear solution of pH ~7.

Protocol 2: CMdex (30 mg) was dissolved in 1.5 ml 0.15M MES buffer pH 5. NHS (100 mg) was added, followed by the immediate addition of 160 mg ECD. After mixing for 1 minute, the reaction mixture was added to hydrazine (0.5 ml of 6.6M at pH 8) while vortexing. The solution was then treated as described above. The product CMdex-Hydr was obtained as 5 ml of a slightly turbid solution (5 ml) of pH ~4 (which became clear at pH 7).

iii) Synthesis of "dendritic molecules" from CMdex: Dendritic molecules were synthesized by reacting CMdex (50 mg) with iminodiacetic acid (580 mg) in the presence of EDC (200 mg) to increase the carboxyl group content. Hydrazine was coupled to the dialyzed product by adding NHS (115 mg), EDC (400 mg) and hydrazine (1.8 ml of 6.6M) as described in section (ii) above, Protocol 2, for CMdex-Hydr. The dendritic product contained 600 hydrazide groups/dextran.

iv) Quantitative determination of dextran (according to Dubois et al, 1956): CMdex-Hydr (50–150 μg dextran range) in 0.8 ml DDW was mixed with 5% phenol solution (0.5 ml in a 100×12 mm glass test tube) and 2 ml concentrated sulfuric acid was added. The reaction mixture was vortexed immediately, and the absorbance at 485 nm was determined 10 minutes later. The concentration was calculated relative to standard CMdex-Hydr solutions.

v) Quantitative determination of hydrazide groups. CMdex-Hydr (50–150 μg dextran range) in i ml 0.05M $NaHCO_3$ was reacted with 250 μg TNBS (25 μl of 10 mg/ml). The absorbance at 500 nm was determined after 10 minutes, and the concentration of hydrazide groups was calculated relative to standard solutions of adipic dihydrazide.

vi) Quantitative determination of carboxyl groups. CMdex-Hydr (3–5 mg dextran range) in 2 ml DDW was titrated with 0.01N NaOH in the presence of phenolphthalein.

vii) Preparation of tyrosylated CMdex. CMdex (55 mg) was dissolved in 2 ml DDW, NHS (7 mg) was added, followed by the immediate addition of EDC (30 mg). After mixing for 1 minute, tyrosine (2 mg) was added while vortexing. The reaction continued for 15 minutes at RT, and the solution was dialyzed against DDW. The molar substitution ratio of tyrosine, as determined from the absorbance at 280 nm in reference to non-tyrosylated CMdex, was 20:1.

viii) Preparation of CDDP complexes with CMdex-Hydr. CDDP in DDW (3 mg/ml, dissolved by slight warming) was mixed with the CMdex-hydrazide derivative at a molar ratio of 500:1. The reaction mixture was placed in a 100° C. water bath for 3–5 min and was further treated as described below in section ix.

ix) Quantitative determination of CDDP (according to Golla et al, 1973): Samples of undialyzed and/or dialyzed CDDP-CMdex-hydrazide complexes of section viii above containing estimated amounts of 3–10 μg of CDDP/0.6 ml DDW were mixed with 0.6 ml OPDA dissolved in DMF (4 mg OPDA/ml DMF, or as indicated). The reaction mixtures were placed in a 100° C.-water bath for 3–5 minutes (as indicated), and the absorbance of the light blue colored solutions formed due to interaction of CDDP (free or reversibly-bound to CMdex) with the OPDA ligand was determined at 730 nm after cooling. The amount of CDDP in the reaction mixture that reacted with OPDA was determined in reference to standard solutions of free CDDP. All CDDP values refer to the OPDA-reactive material, i.e., reversibly-complexed CDDP that is capable of being released from the carrier in favor of the OPDA ligand.

x) TNP modification. The reaction was carried out as described in WO 97/22879, as follows: TNBS dissolved in DDW (10 mg/ml) was reacted at a molar ratio of 200:1 with St, Ova and BSA (1 mg/0.5 ml, 0.2M sodium bicarbonate). After 20 min at room temperature, the pH was adjusted to 7.3 and the products TNP-St, TNP-Ova and TNP-BSA were dialyzed.

CMdex-hydrazide was similarly modified with TNBS to produce TNP-CMdex-hydrazide. CMdex (Mr 250 kDa, 1875 carboxyl groups/dex) was substituted with hydrazido groups according to Protocol 2, and the product was reacted with TNBS at 120:1 molar ratio to form TNP-substituted CMdex-hydrazide. The TNP-CMdex-hydrazide was then reacted with CDDP (2–3 min at 100° C., followed by dialysis to remove uncomplexed Pt) to produce a polymer carrying 60 mol TNP and up to 300 mol complexed Pt/mol CMdex-hydrazide.

(xi) Radioiodination. The $^{125}$I-proteins or $^{125}$I-Tyr-TNP-CMdex-Hydr were produced by reaction with $^{125}$INa as described in WO 97/22879.

Example 1

Biodistribution Studies With Unmodified and TNP-modified BSA, Ova and St

This experiment was conducted with the enzyme-degradable albumins BSA and Ova and the enzyme-resistant protein streptavidin. Groups of 10–12-week old CD-1 male mice were given intravenous infections into the lateral tail vein of the radioiodinated derivatives BSA, Ova, St, TNP-BSA, TNP-Ova and TNP-St (1–2 μCi/mouse). At set time intervals, blood samples were withdrawn from the tail, the mice were killed and their organs were dissected out, blotted dry, weighed and counted for radioactivity. The results are expressed as mean percent of injected radioactivity dose/gram tissue (%/g) or per whole organ (liver).

FIGS. 1A–1B show that, when tested at a time range of 15–120 min, TNP modification of BSA and Ova led to rapid hepatic uptake as compared to unmodified BSA and Ova. However, as described before in WO 97/22879, at the 2-hour time point, both BSA and TNP-BSA were down to <0.3%/g in blood and organs and both Ova and TNP-Ova were down to <0.6%/g, while the biodistribution profile of TNP-St tested at a time range of 15–180 min, was different (FIG. 1C): blood levels for both TNP-St and St were kept high for a longer period of time (22–33%/g) whereas levels in other tissues, including the liver, were low (<10%/g). Elevation of the St in the kidney and TNP-St in the liver was delayed and started to build up at 120 min (23% and 18%/g, respectively), indicating that the TNP modification of proteins increases their uptake by the liver. The slow degradation and processing of Sand TNP-St leads to retardation of uptake and to subsequent accumulation in the target organs (St in kidney and TNP-St in liver).

Figure 2:
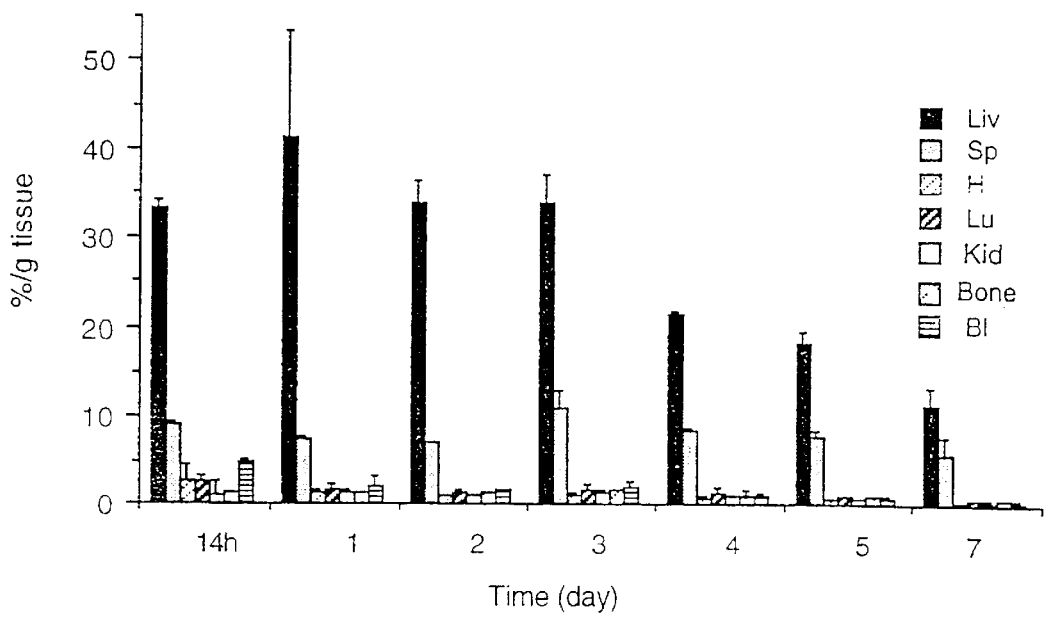
FIG. 2 depicts the biodistribution (%/g tissue) of non-biodegradable iodinated TNP-St in tissues of CD-1 male mice as a function of time (14h-7 days). The levels in blood and six organs are shown, with the lever exhibiting long-term accumulation following injection into mice.

FIG. 2 shows that monitoring the level of TNP-St in different tissues in a period from 14h to 7 days, 33%/g retention of TNP-St was found in the liver at 14 h which increased to 42%/g at 24 h and slowly declined later on.

As already shown by the present inventors (Schechter et al, 1996), TNP modification of proteins or polymers results in high liver accumulation: degradable molecules, e.g., albumins, exhibited short-term accumulation (FIGS. 1A–1B), whereas non-degradable molecules, e.g., enzyme-resistant proteins such as streptavidin (FIGS. 1C, 2), led to long term liver retention.

Example 2

Selection of CDDP-binding Groups

Figure 3:
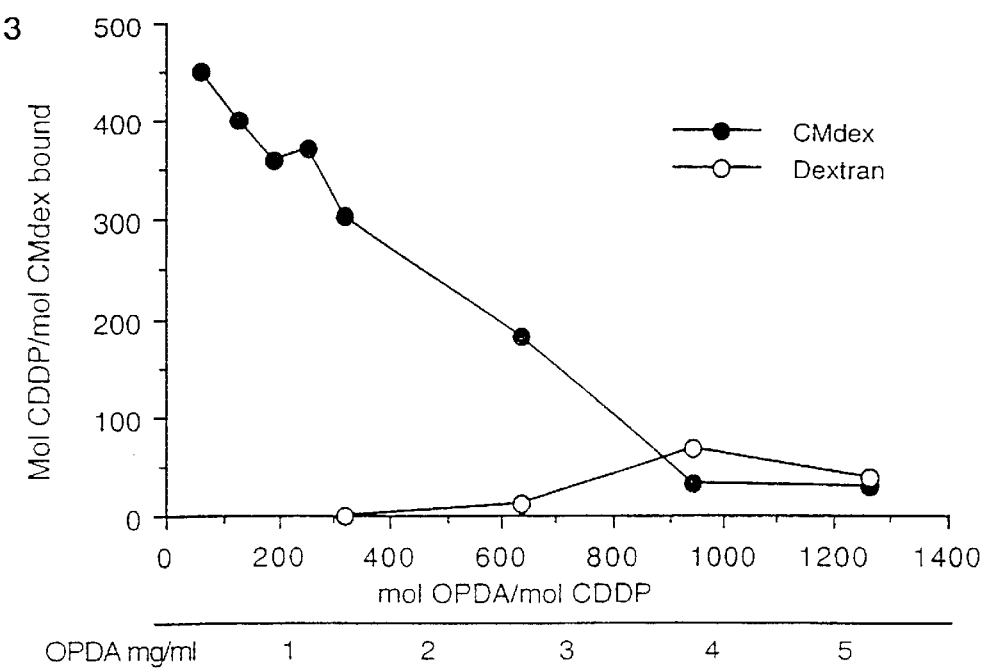
FIG. 3 shows the determination of OPDA concentration required for complete dissociation of CDDP from CMdex. CDDP, CDDP+ dextran or CDDP+ CMdex (6 μg CDDP per sample) were placed at 100° C. for 3 minutes (to form the Pt-CMdex complex) and increasing amounts of OPDA were added. Reaction with OPDA proceeded for 5 more minutes at 100° C. and the absorbance at 703 nm was determined. A concentration of 3.8 mg/ml OPDA (or OPDA to CDDP ratio of 950:1) resulted in complete removal of CDDP from the dextran carrier.

CDDP Complexes of CMdex-hydrazide were characterized in comparison to CDDP complex of CMdex (all derived from dextran Mr-250). The OPDA reagent was used for estimation of the amount of bound CDDP and the relative binding affinities (releasable vs. non-releasable Pt) between CDDP and the different dextran carriers under defined conditions. Since CDDP binds to CMdex in a reversible (releasable) manner, OPDA was first titrated to determine the OPDA/CDDP ratio required for complete removal of CDDP from the CMdex carrier. CDDP was reacted with CMdex at a molar ratio of 500:1 (3 min, 100° C.) to form the CDDP-CMdex complex. Increasing amounts of OPDA were then added (5 min, 100° C.) and the absorbance at 703 nm was determined in comparison to CDDP reacted with unmodified dextran. As shown in FIG. 3, at low OPDA concentration (low OPDA/CDDP ratio), most of the CDDP (6 µg per sample) was bound to CMdex (low A703). Increasing OPDA concentration led to increased release of CDDP from the CMdex backbone in favor of OPDA (higher A703). At 3.8 mg/ml OPDA, or at a molar excess of 950 OPDA/CDDP, all of the Pt was "pilled off" the CMdex carrier in favor of OPDA. No interaction occurred between CDDP and unmodified dextran (high A703 nm, similar to that of free CDDP). This type of Pt determination provides the conditions required for complete removal of reversibly-bound CDDP.

Figure 4:
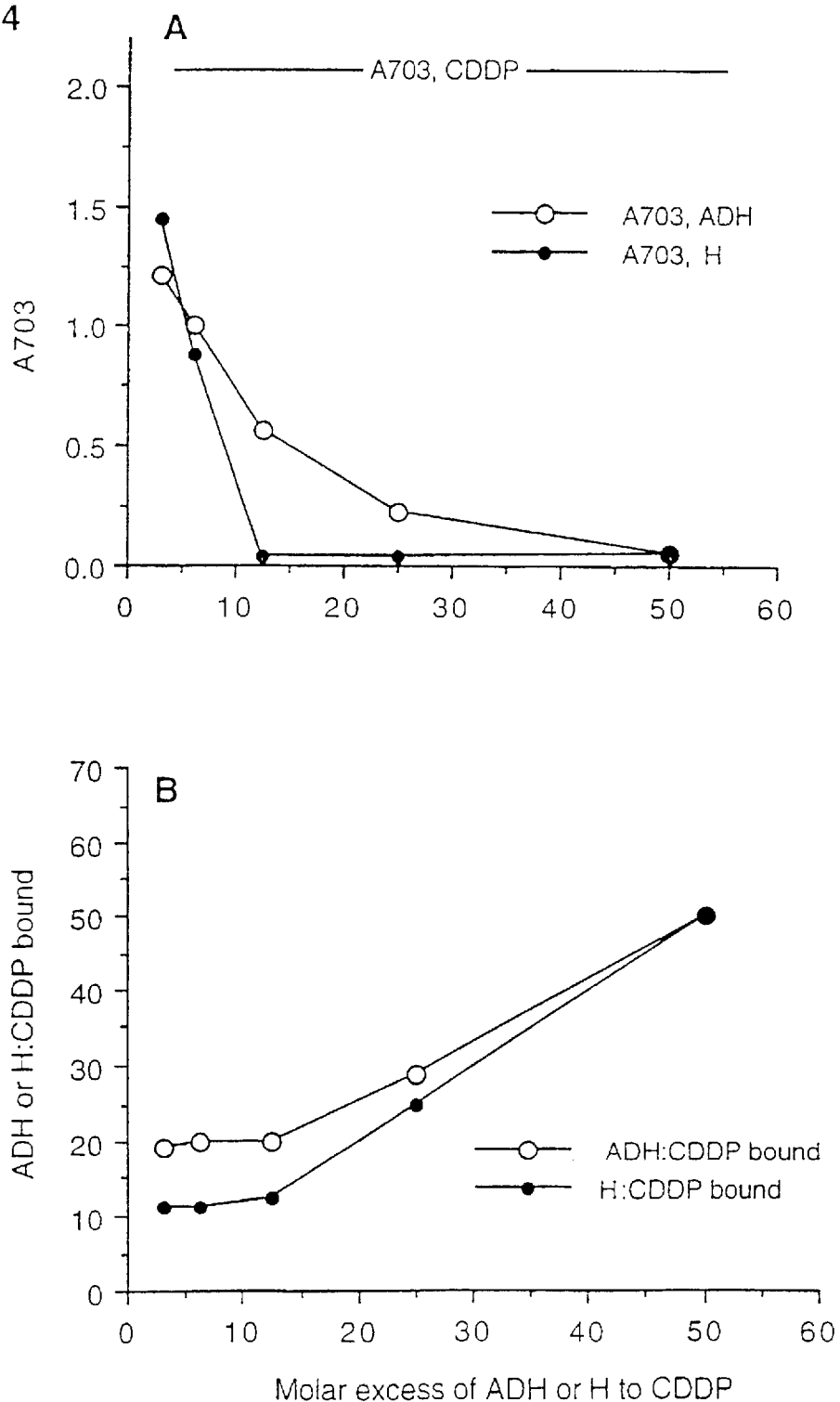
FIGS. 4A–4B show the evaluation of the interaction between CDDP and adipic acid dihydrazide (ADH) or hydrazine (H). Increasing amounts of ADH or hydrazine were reacted for 5 minutes at 100° C. with a constant amount (6 μg) of CDDP when OPDA (4 mg/ml) was added for 5 minutes at 100° C. The absorbance at 703 nm was determined (FIG. 4A).

Several amine-containing compounds were considered as possible high-affinity CDDP ligands for attachment to dexzran. O-phenylenediamine (OPDA), which forms a colored complex with CDDP (absorbance at 703 nm), was found useful in determining relative binding affinities between CDDP and various ligands (Schechter et al, 1989b). Evaluation of two compounds, adipic dihydrazide (ADH) and hydrazine (Hydr), is shown in FIGS. 4A and 4B. ADH or hydrazine were reacted at increasing molar ratios (5 minutes, 100° C.) with CDDP (6 µg), and OPDA 4 mg/ml) was then added (5 minutes, 100° C.). Complete complexing of CDDP to ADH and hydrazine was observed at a molar excess of 50:1 (no color reaction with OPDA). As molar excess of ADH and hydrazine to CDDP decreased, more Pt interacted with OPDA (increased color) up to a leveling-off ratio of 20 ADH:CDDP and 10 hydrazine:CDDP. This is the reason why hydrazine was selected for coupling to CMdex, namely due to its more effective interaction, i.e., lower release of Pt in favor of OPDA and lower ratio of hydrazine:CDDP interaction.

CMdex-hydrazide derived from dextran 250 (1875 carboxyl groups/dextran) was prepared according to Materials and Methods, section (ii), Protocol 1, giving rise to a highly substituted product, with 700 hydrazide groups per dextran or 37% of total carboxyl group content (Table 4). The pH of the product solution after HCl treatment and dialysis was around 7, indicating low carboxyl content. This was verified by NaOH titration which showed that only 20% of the total carboxyls (370 mol/mol CMdex) were free, i.e., 800 carboxyl groups that were not substituted by hydrazide groups, were blocked.

CMdex-hydrazide derived from the same dextran 250 but prepared according to Materials and Methods, section (ii), Protocol 2, was less effective in terms of hydrazine substitution and contained 240 hydrazide groups per dextran (13% of carboxyls), but blocking of unsubstituted carboxyl groups did not occur, i.e., 1600 carboxyls (86%) were free. The pH of this product following HCl treatment and dialysis was around 4.

Blocking of carboxyl groups during synthesis according to Protocol 1 with EDC alone could be attributed to cross-linking by hydrazine, but different synthetic procedures showed that increasing hydrazine molar excess to prevent cross-linking was ineffective. Blocking could, therefore, occur by ECD itself, which does not take place in the presence of NHS (Protocol 2). The protecting effect of NHS on EDC blocking of carboxyls could be demonstrated when CMdex alone (no hydrazine, was subjected to treatment with EDC in the presence or absence of NHS; only 40–46% of the carboxyl groups were free when NHS was left out, whereas 80–90% free carboxyls were free when NHS was included (Table 4).

TABLE 4

Synthesis of CMdex-hydrazide

| | CMdex (mg) | EDC (mg) | NHS (mg) | Hydrazine (mmol) | H/dex (%) | COOH/dex (%) |
|---|---|---|---|---|---|---|
| 1[a] | 30 | 160 | — | 2.5 | 37.8 [700:1] | 20 |
| 2[b] | 30 | 160 | 100 | 3.3 | 13 [240:1] | 86 |
| 3 | 10 | 50 | — | — | — | 40 |
| 4 | 10 | 50 | 60 | — | — | 80 |
| 5 | 10 | 100 | — | — | — | 46 |
| 6 | 10 | 100 | 30 | — | — | 90 |

[a]Protocol 1; [b]Protocol 2

The two synthetic procedures described in Table 4 gave rise to two different CMdex-Hydr products. An experiment, which results are presented in Table 5, was designed to characterize these two CMdex-Hydr preparations with respect to their irreversible (strong) CDDP binding. CDDP was reacted with dextran, CMdex and CMdex-Hydr, as described above, to form the corresponding CDDP-dex complexes, and part of each reaction mixture was dialyzed against DDW (4 hours, 2×2L). OPDA reactivity was determined on undialyzed and on dialyzed material. As shown in Table 5, when CDDP was reacted with dextran (Mr-250) at a molar ratio of 500:1 (3 min at 100° C.), all of the CDDP (99%) was OPDA-reactlive (4 mg/ml OPDA) before dialysis and none after dialysis.

TABLE 5

Characterization of CMdex-H-Pt Complexes
Dex 250. CDDP:dex = 500:1 (100 μg Pt)

| Dextran Derivative | CDDP before Dialysis (%) | | CDDP after Dialysis (%) | | CDDP: CMdex Bound (molar ratio) | |
|---|---|---|---|---|---|---|
| | OPDA Reactive[a] | Irreversibly Bound[b] | OPDA Reactive[c] | Non-bound[d] | Reversibly Bound | Irreversibly Bound |
| Dextran | 99 | 1 | 1 | 98 | 5:1 | 5:1 |
| CMdex | 95 | 5 | 87 | 8 | 435:1 | 25:1 |
| CMdex-H Protocol 1 (700H/dex) | 90 | 10 | 3 | 87 | 15:1 | 50:1 |
| CMdex-H Protocol 2 (280H/dex) | 54 | 46 | 4 | 50 | 20:1 | 230:1 |
| CMdex-H Protocol 2 (100H/dex) | 63 | 37 | 24 | 39 | 120:1 | 185:1 |
| CDDP 100 | 100 | 0 | 1 | 99 | | |

[a]Complex was formed by reacting CDDP and dextran derivative at 100° C. for 3 min and testing samples with OPDA at 100° C. for 5 min. Represent percent reversibly + non-reversibly bound CDDP.
[b]Values represent the difference between 100% CDDP input and % OPDA-reactive CDDP.
[c]Reversibly bound CDDP.
[d]Values represent the difference between OPDA reactive CDDP before and after dialysis.

This indicates that no binding occurred between CDDP and unmodified dextran and that dialysis was complete (no non-specific binding). When reacted with CMdex, a major fraction of the CDOP was reactive with OPDA before dialysis (95%). This means that either none of the CDDP was complexed and/or the CDDP was bound in a reversible manner. After dialysis, 87% reacted with OPDA, i.e., 87% (435 Pt/dex) of the CDDP was complexed to CMdex in a reversible manner (5% was irreversibly bound, and 8% was free and removed during dialysis). When CDDP was reacted with CMdex-Hydr (Protocol 1; 700 Hydr/dex), 90% was OPDA-reactive before dialysis, i.e., 10% was irreversibly bound (50 Hydr/dex). After dialysis, only 3% was OPDA-reactive. This means that CMdex-Hydr prepared according to Protocol 1 did not bind CDDP effectively neither in the reversible nor in the non-reversible form. When CDDO was reacted with CMdex-Hydr, Protocol 2 (280 Hydr:dex), 54% was OPDA-reactive before dialysis, i.e., 46% was irreversibly bound (230 Hydr:dex). After dialysis, only 4% was OPDA-reactive, i.e., none of the CDDP was bound in a reversible manner. A CMdex-Hydr derivative of lower Hydr content (100 Hydr/dex) contained a lower fraction of stably-bound CDDP (37%) and a higher fraction of reversibly-bound CDDP (24%). It is concluded that: (a) contrary to the expected, bindinof CDDP to the hydrazide-rich product was low, whereas binding to the hydrazide-low product, relative to hydrazine content, was good; (b) above a certain hydrazine substitution ratio, and despite the expected abundance of free carboxyl groups, there is no reversible binding of CDDP; and (c) reversibly-bound CDDP can be determined only in the dialyzed complex, whereas irreversibly-bound CDDP can be determined only on the undialyzed complex. It should also be noted that there was no simple direct correlation between the number of hydrazide groups and CDDP binding, the later being often higher.

In order to further determine the reversibly and irreversibly-bound Pt in CDDP-CMdex and CDDP-CMdex-hydrazide complexes, CDDP (60 μg), CDDP+ dextran, CDDP+ CMdex or CDDP+CMdex-Hydr complexes were each dialyzed against DDW (10 ml/sample) for 12 hours, and OPDA-reactive CDDP was determined in the dialyzed samples, as well as in the dialysis water. In this type of experiment, where relatively low amounts of CDDP are used and a long dialysis period is required, a fraction of the total free CDDP is lost (around 40%) due to non-specific complexing of CDDP to surrounding components such as dialysis bag, glass, etc.

Figure 5:
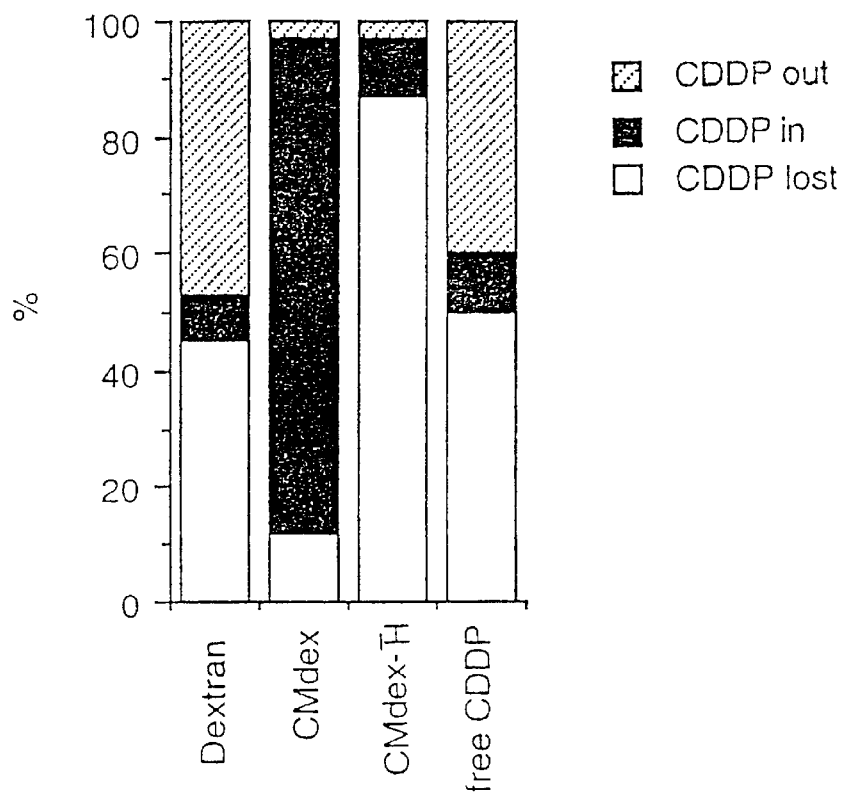
FIG. 5 shows the determination of reversibly and irreversibly bound Pt in CMdex and CMdex-Hydr complexes. CDDP (60 μg), CDDP+dextran, CDDP+CMdex or CDDP+CMdex-Hydr reacted for 3 min at 100° C. at a molar ratio of 500:1. Each sample was then dialyzed for 12 hours in 1 ml volumes against 10 ml DDW. Samples from the dialyzed material (in) and the dialysis DDW (out) were removed for interaction with OPDA (5 minutes at 100° C.), and the absorbance at 703 nm was determined. Most of the CDDP complexed to CMdex was reversibly bound, whereas most of the CDDP bound to the CMdex-Hydr was irreversibly bound. CDDP "lost" means CDDP not found by OPDA reaction inside or outside the dialysis bag, i.e. it could be lost or irreversibly bound.

As shown in FIG. 5, Pt determined for free CDDP or CDDP reacted with dextran was 45–50% lower than the original Pt input. Only 12% loss of Pt was observed with the CDDP-CMdex complex. This can be expected since CDDP was CMdex-complexed and most of it (85%) was retained as reversibly bound Pt within the dialyzed material. This is in accord with our previous observation that CDDP complexed to CMdex is protected against irreversible interaction with body constituents (proteins, etc.) when injected into mice (Schechter et al, 1989a). When CDDP was complexed to CMdex-H (prepared according to Protocol 2), only a total of 14% of the CDDP input was found by measuring samples from inside and outside the dialysis bag. Assuming that Pt loss in this case is no higher then with the CMdex complex, it can be calculated that out of the 86% missing Pt, about 75% was irreversibly bound.

Example 3

Metal Targeting to Tissues: Biodistribution Studies Eith Unmodified CDDP-CMdex-hydrazide (Pt-CMdex) and TNP-modified CDDP-CMdex-hydrazide (Pt-TNP-CMdex)

Figure 6:
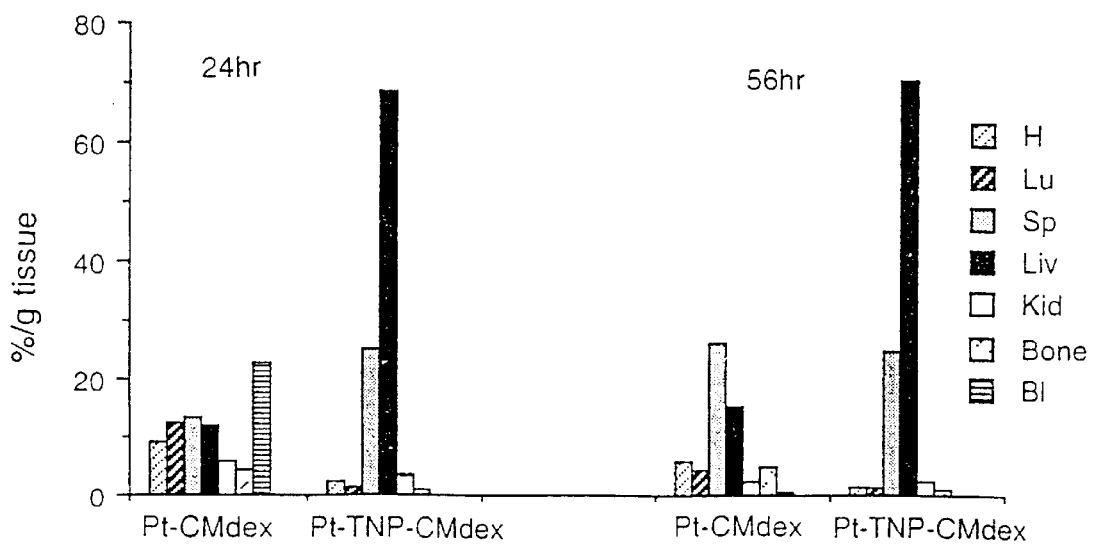
FIG. 6 shows the biodistribution (%/g tissue) of CMdex-Pt before and after TNP modification at 24 and 56 hours in various tissues. TNP modification resulted in specific long-term liver accumulation following injection of the TNP-modlfied CMdex-Hydr completed to CDDP.

The system used for demonstrating Pt targeting to the liver consisted of complexes between CDDP and hydrazido-substituted polymers. CDDP can form high affinity, non-dissociable and pharmacologically inert complexes with certain polymers (Howe-Grant et al, 1980) such as dextran-hydrazide. Modifying dextran-hydrazide with the liver marker trinitrophenyl groups (TNP), as described in PCT Patent Appln. No. WO 97/22879 of the present applicants, leads to selective delivery to the liver with levels of up to 70 percent of the injected dose per gram tissue (%/g) or up to 80% of the total dose accumulated in the whole liver. This is based on studies (Schechter et al, 1996) showing that TNP modification of proteins or polymers resulted in high liver accumulation: degradable molecules, e.g., albumin, exhibited short-term accumulation (FIGS. 1A, 1B), whereas non-degradable molecules, e.g., enzyme-resistant proteins such as streptavidin or dextran-hydrazide, led to long term liver retention (FIGS. 1C, 2, 6). Since accumulation is correlated with marker density, macromolecules can serve as targeting vehicles for diagnostic agents, provided their content of functional groups is high enough to carry both a sufficient quantity of marker molecules and the delivered agent.

Experiments were conducted on PD delivery to mouse liver to demonstrate (a) the ability for loading a substantial amount of the contrast agent onto the carrier; (b) high specific accumulation of the complex in the target tissue; and (c) detectability of the agent loading by standard X-ray mammographic equipment.

For targeting the CDDP-CMdex-hydrazide complex to the liver via TNP, trace-tyrosylated CMdex (20 tyrosyl/dex) prepared according to Materials and Methods, section vii, was used to enable radioiodination with iodine-125 (Materials and Methods, section xi). Tyrosyl-CMdex was substituted with hydrazine and the Tyr-CMdex-hydrazide was treated with 120 mol TNBS/mol CMdex to obtain a TNP-modified CMdex-hydrazide containing 60 mol covalently bound TNP/mol dex (after dialysis). CDDP was complexed to the product (500:1 molar ratio, 3 min at 100° C. followed by dialysis). A control complex was similarly prepared but without the TNP.

Mice were injected intravenously with 50 μg of the radioiodinated materials (Pt-TNP-CMdex and Pt-CMdex) and the mice were killed at 24 and 56 hours. Radioactivity in blood and organs was monitored in reference to tissue weight and biodistribution in terms of percent of total injected dose/gram tissue (%/g) was determined. As shown in FIG. 6, levels of $I^{125}$-CMdex-Pt (no TNP) in most tissues were in the range of 3–12%/g (22%/g in blood) at 24 hours after injection and were lower in most organs after 56 hours. The biodistribution pattern of the TNP-carrying complex was different: levels in blood and most organs was below 2%/g, except for the liver, where values reached 66%/g (82%/total liver) after 24 hours and were still at the same range at 56 hours. Spleen levels were also increased (23%/g).

The biodistribution and liver accumulation of radioiodinated TNP-dextran hydrazide loaded with Pt, at 24 and 56 hours following intravenous injection into CD-1 mice, is shown in FIG. 6.

In another experiment, the same complex (150 μg) was similarly injected (non-radioiodinated), and 12 hours later, the mice were sacrificed and their livers were removed. Tissue extracts were prepared by homogenizing organs in 5×vol of 0.1N NaOH/tissue weight for 60 seconds, followed by centrifugation at 12000×g. Supernatants were subjected to X-ray fluorescence (XRF) analysis. Standards were prepared in a matrix identical to that of the samples (i.e., normal tissues) to account for possible matrix interference. Administration of the complex (130 μg complexed Pt) resulted in liver accumulation of 70%/g tissue, i.e., about 90 μg Pt metal/gram liver (no figure), a value which falls within the required range for contrast enhancement, as described below.

A mouse injected with such a preparation was subjected to X-ray mammography, along with a mouse which had been injected by the same amount of dextran solution with no Pt. As shown in FIGS. 7A and 7B, the liver of the Pt-targeted mouse is of a darker shade and is clearly delineated (FIG. 7A), whereas that of the control mouse is lighter and cannot be distinguished from other organs (FIG. 7B).

CDDP binds to CMdex in a reversible manner, i.e., it is released in biological systems in vivo in favor of ligands exhibiting a higher affinity towards Pt. CDDP complexes of CMdex are toxic above a certain dose, with the toxicity being correlated with the dextran molecular weight. Complexes of CMdex T-40 are similar to that of free CDDP in their activity, whereas complexes of higher dextrans are more toxic.

The CDDP-CMdex-Hydr product (Protocol 2) prepared according to the present invention was non-toxic when tested by injecting the dialyzed complex at two doses 350 μg (13.5 mg/kg) and 630 μg (23.7 mg/kg) complexed CDDP. This is a striking advantage over the use of CMdex-type polymer (T-250) that contains no hydrazide groups which is shown to have high toxicity of CMdex-CDDP complex (toxic already at 4 mg/kg) (Schechter et al, 1989b).

Higher TNP and CDDP load can be achieved by forming a "dendrite" molecule of increased carboxyl groups content; CMdex reacted with iminodiacetic acid resulted in a molecule that could carry 150 mol TNP and up to 600 mol Pt/mol dextran-hydrazide, an advantageous product in view of its increased marker content and higher metal-load. Increasing the TNP ratio facilitates liver accumulation, whereas the high metal content enables the use of lower injected carrier doses.

In order to assess experimentally the minimal required dose of contrast agent and the feasibility of its selective delivery to the tissue, the contrast agent concentration level required for imaging was calculated from compiled X-raabsorption cross-section data and the sensitivity of standard X-ray detection techniques. To further assess these estimates, a Plexiglas phantom having various sized compartments and containing platinum chloride sample solutions of various concentrations was imaged by both CT (computed tomography) and standard film-based mammography.

Figure 8:
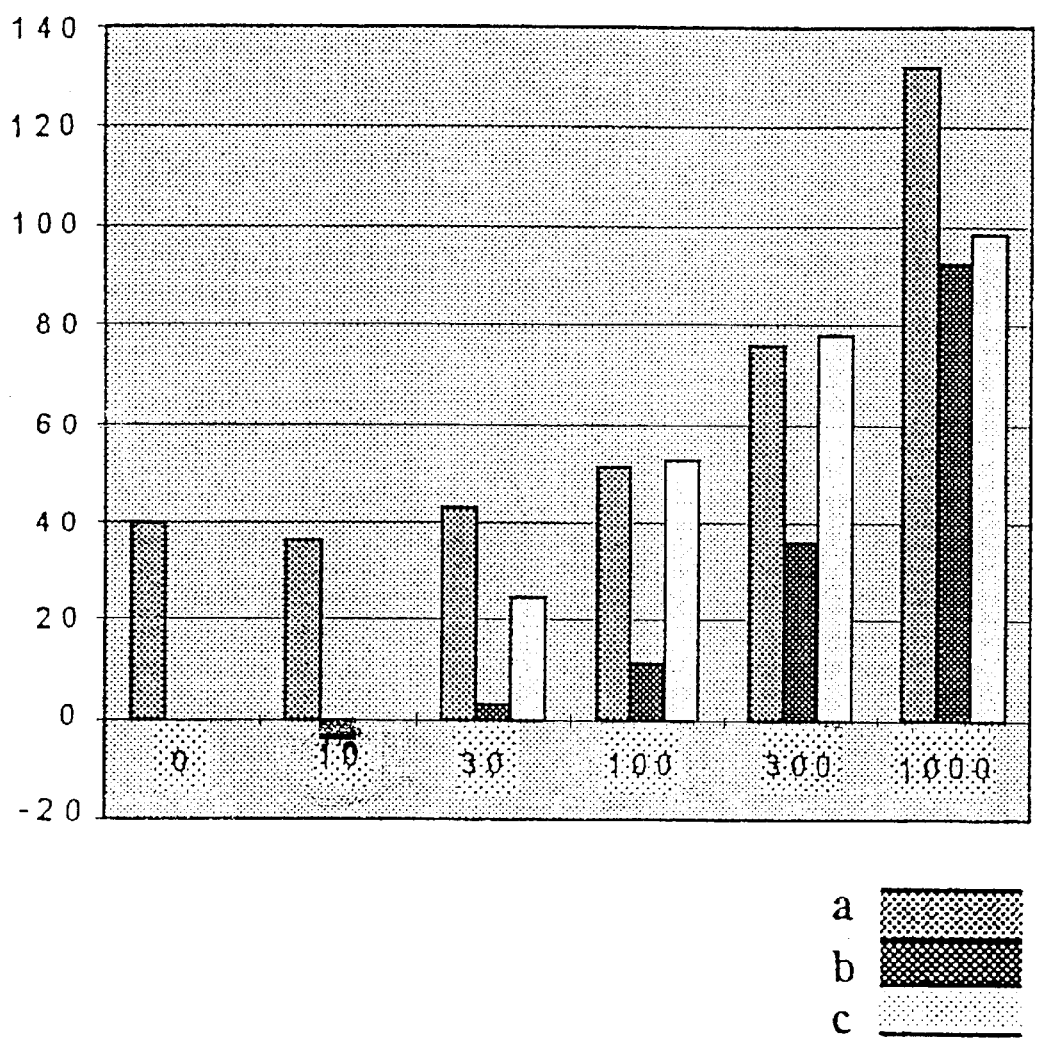
FIG. 8 shows a computed tomography (CT) image of a 1 mm-thick slice through the Plexiglas phantom. The various square compartments contain Pt, in aqueous solution, at concentrations (left to right) 0, 10, 30, 100, 300 and 1000 μg/ml. The corresponding average gray levels, measured within the circled area, are: 39.9, 36.1, 43.0, 51.3, 75.7 and 132.1. The effect of the Pt X-ray attenuation is clearly seen and can be quantified from 100 μg/ml on. A thumbnail top view of this phantom is seen at the bottom left of the image. The dark oval shaped areas in the squares are air bubbles, excluded in the analysis. This data is presented in graphic form in FIG. 9.
Figure 9:
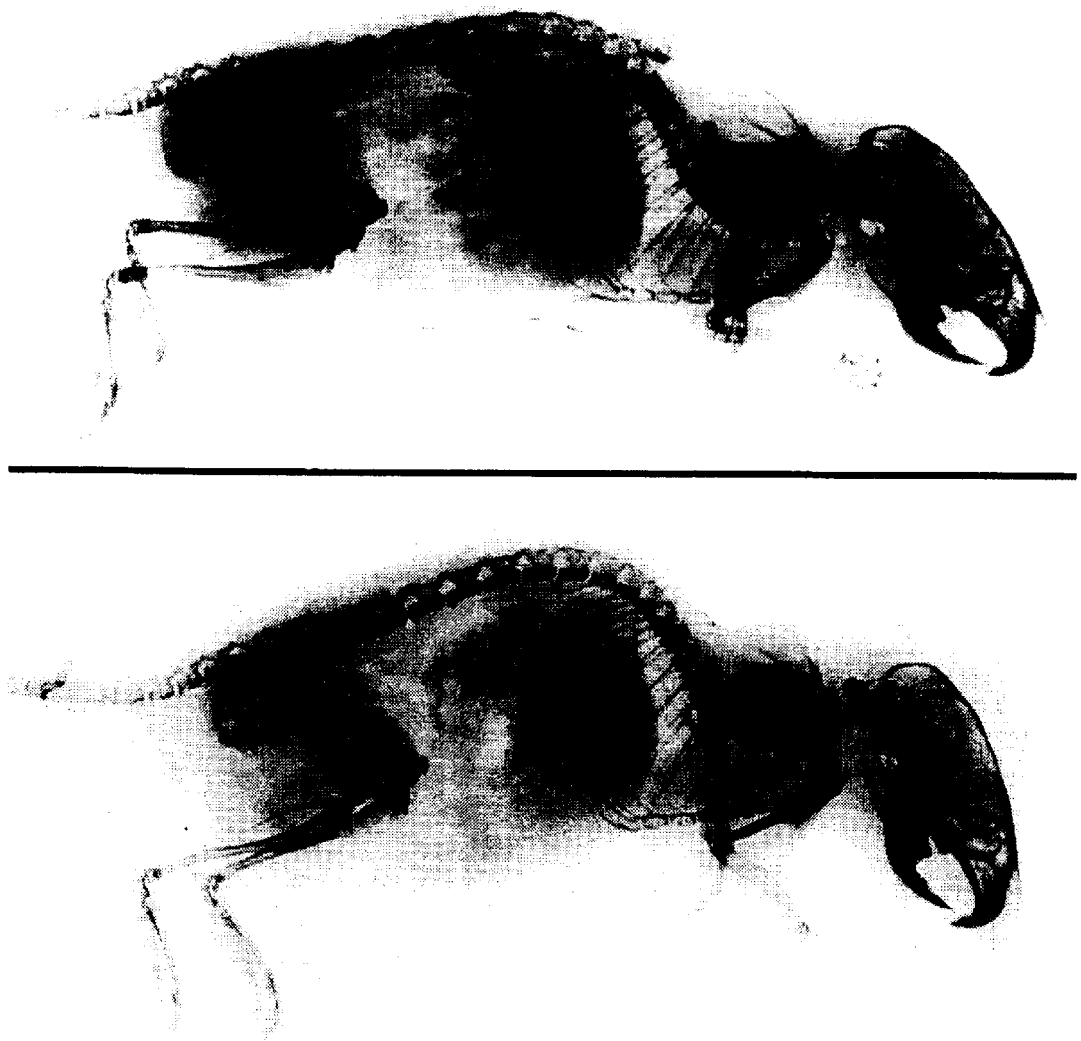
FIG. 9 is a graphical presentation of the X-ray attenuation in the 0–1000 μg/ml Pt $Na_2PtCl_6$ solutions shown in FIG. 7. Each group of bars corresponds to a given compartment of the phantom: a. actual CT values (dashed bars); b. normalized values (0 concentration value subtracted; dark bars); c. logarithmic presentation of b (open bars). At 100 μg/ml sample, the increased X-ray attenuation is clearly detectable.

An example of a CT scan through the phantom, showing the X-ray absorption by solutions of different Pt concentrations, is shown in FIG. 8. The results, summarized in FIG. 9, clearly support the theoretical estimate of about 100 μg/ml required for a detectable contrast change in CT. Similar results were obtained by film-based mammography.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A delivery system for delivering a contrast agent to a target organ or tissue for X-ray imaging, said delivery system comprising a non-toxic conjugate or complex of:
   (i) a contrast agent selected from the group consisting of a compounds having an element with a property of an abrupt change in its X-ray attenuation coefficient within the energy range of 10 to 30 keV and compounds having an element with a property of an abrupt change in its X-ray attenuation coefficient within the energy range above 30 keV;
   (ii) a non-toxic macromolecular carrier containing a high loading of said element through high affinity binding groups that prevent release of said element.

2. The delivery system according to claim 1, wherein said non-toxic macromolecular carrier is selected from the group consisting of non-toxic liposomes, natural polymers and synthetic polymers.

3. The delivery system according to claim 1, wherein said non-toxic macromolecular carrier is a natural or synthetic polymer carrying high affinity metal-binding groups selected from the group consisting of dicarboxylic acids, iminodiacetic acid, ethylenediaminotetraacetic acid (EDTA), diethylenetriaminopentaacetic acid (DTPA), hydroxyquinoline, hydroxamic acid, thiol, hydrazido, piperazine and combinations thereof.

4. The delivery system according to claim 3, wherein said natural or synthetic polymer is selected from the group consisting of dextran, modified dextran, poly-L-lysine, polyglutamic acid and polymethacrylic acid.

5. The delivery system according to claim 4, wherein said modified dextran is carboxymethyldextran carrying binding groups selected from the group consisting of hydrazido, iminodiacetic acid and combinations thereof.

6. The delivery system according to claim 1, wherein macromolecular carrier in said conjugate or complex is linked to a specific tissue marker.

7. The delivery system according to claim 6, wherein said specific tissue marker is the liver marker 2,4,6-trinitrophenyl group (TNP).

8. The delivery system according to claim 1, wherein the element with a property of an abrupt change in its X-ray attenuation coefficient within the energy range of 10 to 30 keV has an atomic number in the range of 33 to 50.

9. The delivery system according to claim 8, wherein said element is Zr.

10. The delivery system according to claim 1, wherein the element with a property of an abrupt change in its X-ray attenuation coefficient at an energy range above 30 keV has an atomic number above 50.

11. A diagnostic X-ray imaging method, comprising the steps of
   administering to a patient an effective amount of a delivery system, wherein said delivery system comprises a conjugate or complex of:
   (i) a contrast agent selected from the group consisting of (a) a compound having a heavy metal with an atomic number in the range of 75 to 92, and (b) a compound having an element with a property of an abrupt change in its X-ray attenuation coefficient within the energy range used for radiography, and
   (ii) a non-toxic macromolecular carrier containing a high loading of said heavy metal of (a) or said element of (b) through high affinity binding groups that also prevent release of said heavy metal or said element, said macromolecular carrier of said conjugate or complex being optionally linked to a specific tissue marker molecule;

X-ray imaging the patient; and
   reading the X-ray of the patient.

12. The method according to claim 11, wherein said delivery system comprises a conjugate or complex of:
   (i) a compound having a heavy metal with an atomic number in the range of 75–92; and
   (ii) a non-toxic macromolecular carrier containing a high loading of said heavy metal with an atomic number in the range of 75–92 through high affinity binding groups that also prevent release of said heavy metal with an atomic number in the range of 75–92, said macromolecular carrier of said conjugate or complex being optionally linked to a specific tissue marker molecule.

13. The method according to claim 12, wherein said heavy metal having an atomic number in the range of 75 to 92 is selected from the group consisting of Pt, Au and Tl.

14. The method according to claim 13, comprising administering a complex of a contrast agent consisting of a non-radioactive Pt compound and carboxymethyldextran high loaded with hydrazido groups.

15. The method according to claim 14, wherein said complex is a cisplatin-carboxymethyldextran-hydrazide complex.

16. The method according to claim 15, wherein said cisplatin-carboxymethyldextran-hydrazide complex has many free carboxyl groups and few hydrazido groups.

17. The method according to claim 11, wherein the patient is imaged by a X-ray imaging technique selected from mammography, radiography and computer tomography (CT).

18. The method according to claim 11, wherein said delivery system comprises a conjugate or complex of:
   (i) a contrast agent selected from a compounds having an element with a property of an abrupt change in its X-ray attenuation coefficient within the energy range used for radiography; and
   (ii) a non-toxic macromolecular carrier containing a high loading of said element through high affinity binding groups that also prevent release of said element, said macromolecular carrier of said conjugate or complex being optionally linked to a specific tissue marker molecule.

19. The method according to claim 18, wherein said contrast agent consists of a compound having an element with a property of an abrupt change in its X-ray attenuation coefficient within the 10 to 30 keV energy range.

20. The method according to claim 19, wherein the element with a property of an abrupt change in its X-ray attenuation coefficient within the energy range of 10 to 30 keV has an atomic number in the range of 33 to 50.

21. The method according to claim 20, wherein said element is Zr.

22. The method according to claim 18, wherein said contrast agent consists of a compound having an element with a property of an abrupt change in its X-ray attenuation coefficient in the energy range above 30 keV.

23. The method according to claim 22, wherein the element with a property of an abrupt change in its X-ray attenuation coefficient at an energy range above 30 keV has an atomic number above 50.

24. The method according to claim 18, wherein said X-ray imaging is by an imaging technique selected from mammography, radiography and computer tomography (CT) and the element with a property of an abrupt change in its X-ray attenuation coefficient within the energy range used for radiography has an attenuation threshold that is within the X-ray energy range used for said specific imaging technique selected.

25. The method according to claim 24, wherein the images obtained from said X-ray imaging are obtained from two parts of the X-ray energy spectrum, one above the attenuation threshold and one below the attenuation threshold, and the images are used to digitally generate a difference image having superior contrast.

26. The method according to claim 25, wherein said difference image is generated by filtering the X-ray radiation impinging on the patient.

27. The method according to claim 11, wherein said macromolecular carrier in said conjugate or complex is linked to a specific tissue marker.

28. The method according to claim 27, wherein said specific tissue marker is the liver marker 2,4,6-trinitrophenyl group (TNP).

29. An X-ray imaging method used for a purpose selected from the group consisting of diagnosing the presence of a tumor, prognosticating the effectiveness of a chemotherapy protocol in the treatment of cancer of the patient and determining the effectiveness of a therapy treatment of cancer of the patient comprising the steps of administering to a patient an effective amount of a delivery system, wherein said delivery system comprises a conjugate or complex of:
  (i) a contrast agent selected from the group consisting of (a) a compound having a heavy metal with an atomic number in the range of 75 to 92, and (b) a compound having an element with a property of an abrupt change in its X-ray attenuation coefficient within the energy range used for radiography, and
  (ii) a non-toxic macromolecular carrier containing a high loading of said heavy metal of (a) or said element of (b) through high affinity binding groups that also prevent release of said heavy metal or said element, said macromolecular carrier of said conjugate or complex being optionally linked to a specific tissue marker molecule;

X-ray imaging the patient; and reading the X-ray of the patient.

\* \* \* \* \*